United States Patent
Lilly et al.

(10) Patent No.: US 6,953,471 B1
(45) Date of Patent: Oct. 11, 2005

(54) CANNULA WITH FLEXIBLE REMOTE CABLE FILTER DEPLOYMENT

(75) Inventors: Richard Lilly, San Jose, CA (US); Richard O. Murphy, Sunnyvale, CA (US); Peter Thornton, Los Altos, CA (US); Timothy J. Wood, Wilmington, MA (US)

(73) Assignee: Edwards Lifesciences Corporation, Irvine, CA (US)

( * ) Notice: Subject to any disclaimer, the term of this patent is extended or adjusted under 35 U.S.C. 154(b) by 287 days.

(21) Appl. No.: 10/071,680

(22) Filed: Feb. 7, 2002

(51) Int. Cl.[7] ............................................... A61M 29/00
(52) U.S. Cl. ..................................................... 606/200
(58) Field of Search ........................ 606/200, 113, 127

(56) References Cited

U.S. PATENT DOCUMENTS

| | | |
|---|---|---|
| 5,662,671 A | 9/1997 | Barbut et al. |
| 5,846,260 A | 12/1998 | Maahs |
| 5,911,734 A | 6/1999 | Tsugita et al. |
| 5,989,281 A | 11/1999 | Barbut et al. |
| 6,007,557 A | 12/1999 | Ambrisco et al. |
| 6,231,544 B1 | 5/2001 | Tsugita et al. |

*Primary Examiner*—(Jackie) Tan-Uyen T. Ho
(74) *Attorney, Agent, or Firm*—Edwards Lifesciences

(57) ABSTRACT

A medical device for filtering embolic material. The device comprises a cannula having a lumen, the lumen communicating with a port at the distal end. A port is located on an outer surface of the cannula adjacent a distal region of the cannula, the port having a passage extending distally and communicating with a distal opening in the port. A filter is removably insertable through the passage of the port, the filter comprising a flexible tubular member, a flexible shaft extending through the tubular member, and an expansion frame mounted on the distal end of the shaft. A filter mesh attached to the expansion frame. The expansion frame may optionally include a cantilever beam to support the far end of the frame, and in certain cases the cantilever beam is flexible to avoid scraping the vessel wall during use. Methods of use are also described.

5 Claims, 10 Drawing Sheets

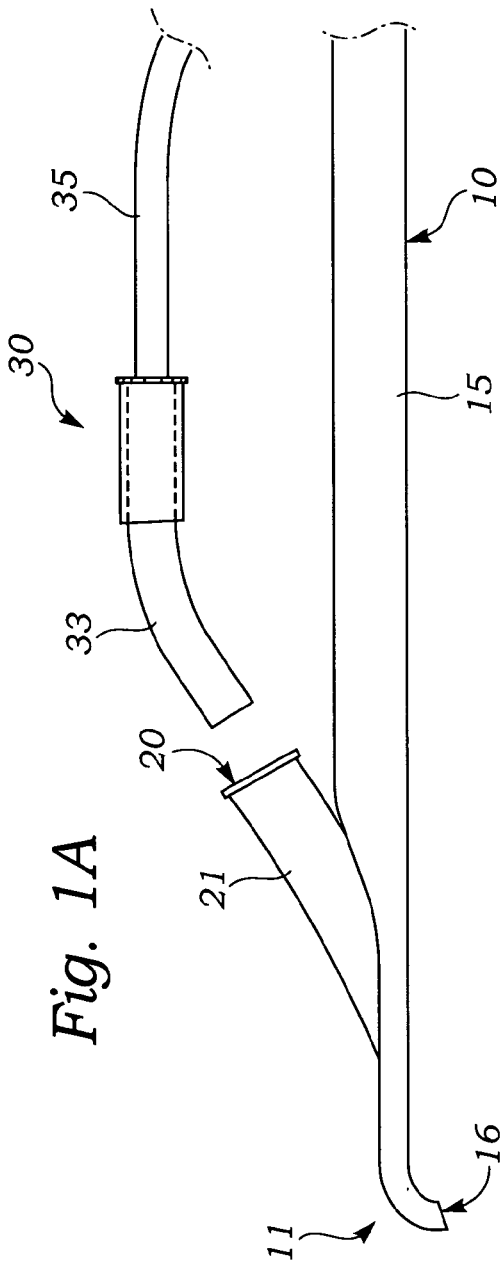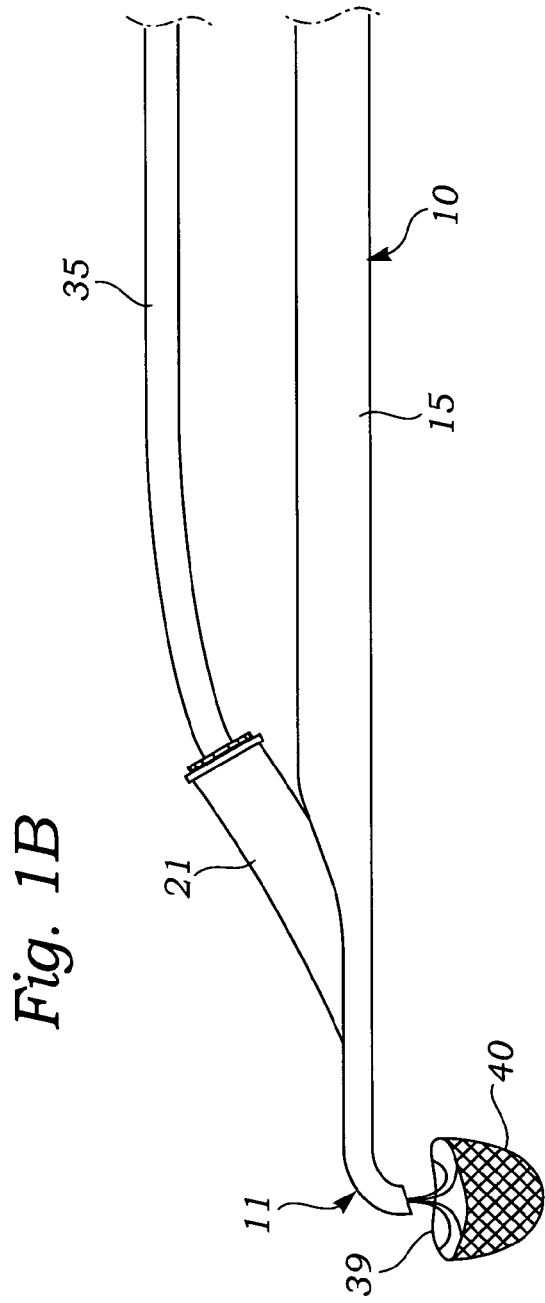

US 6,953,471 B1

CANNULA WITH FLEXIBLE REMOTE CABLE FILTER DEPLOYMENT

FIELD OF THE INVENTION

The present invention relates generally to blood filter devices for temporary placement in a blood vessel to capture embolic material, and particularly to a cannula with a filter device for placement in a blood vessel to perfuse the vessel and to entrap embolic material in the vessel. The filter device includes a flexible cantilever beam that allows use without scraping the blood vessel.

BACKGROUND OF THE INVENTION

Cardiopulmonary bypass is often used during cardiovascular surgeries, including coronary artery bypass grafting, valvular repair or replacement, septal defect repair, and pulmonary stenosis surgeries. To establish cardiopulmonary bypass, an arterial cannula is typically introduced into the aorta to deliver oxygenated blood from a bypass-oxygenator machine.

It is known that embolic material, including tissue debris, calcium, atheromatous plaque, and/or thrombi are often generated during cardiovascular procedures, especially during clamping and unclamping of the aorta. Such embolic material often travels downstream to small vessels of vital organs, causing tissue ischemia or infarction. For example, transient ischemic attack (TIA) and cerebral infarction (stroke) are common complications of coronary artery bypass grafting surgeries.

To reduce the risk of distal embolism, arterial cannulas which include a blood filter device have been developed, allowing the filter to capture loose embolic material once the cannula is introduced into the vessel. Generally such devices include an expandable frame, such as an inflation seal or an umbrella frame, and a filter mesh attached to the frame, the mesh being adapted to capture embolic material of a predetermined minimum size. The frame may be attached externally to the distal end, or alternatively, it may be retractably deployed from a lumen within the cannula.

However, there are several disadvantages associated with the use of a cannula with such a filter device. First, the expansion frame is often rigid. When the filter is expanded in a vessel, any movement of the cannula will cause displacement of the filter within the vessel, and cause the frame to scrape against the vascular wall, resulting in vascular damage, e.g., dislodgement of plaque, hemorrhage, or dissection. Second, the proximal end of the filter device is often rigid and contributes to crowding of the surgical field, especially in minimally invasive procedures.

Thus, there is a need for a filter device for use with an arterial cannula that minimizes the rigidity of the filter device and the expansion frame of the filter, thereby reducing the risk of vascular wall injury.

SUMMARY OF THE INVENTION

The invention includes medical devices for filtering embolic material. In one embodiment the device comprises a cannula having a proximal end, a distal end, and a lumen therebetween, the lumen communicating with a port at the distal end. A port is located on an outer surface of the cannula adjacent a distal region of the cannula, the port having a passage extending distally and communicating with a distal opening in the port. A filter is removably insertable through the passage of the port, the filter comprising a flexible tubular member, a flexible shaft extending through the tubular member, and an expansion frame mounted on the distal end of the shaft. The frame is expandable between a contracted condition and an expanded condition. The frame is deployable through the distal opening of the passage of the port. A distal end of the shaft is insertable through the passage of the port while a proximal end of the shaft extends outside the port. A filter mesh attached to the expansion frame.

In use, the cannula is inserted into a vessel. The filter is inserted into the port on the cannula. The filter is advanced through the passage into the vessel, and is deployed within the vessel. A procedure is then performed on the patient upstream of the filter, e.g., cross-clamping for CPB, CPB, valve repair, myocardial ablation, etc., wherein the procedure dislodges embolic material. Embolic material is captured by the filter. The filter and captured embolic material is then removed from the vessel. It will be understood that the filter may be deployed before or after the onset of cardiopulmonary bypass.

In another embodiment, the invention includes a filter comprising a tubular member and a shaft adapted to extend through the tubular member. An expansion frame is mounted on the distal end of the shaft, the frame expandable between a contracted condition and an expanded condition. The frame comprises a flexible ring and optionally a flexible cantilever beam that slideably extends from a distal end of the shaft and bisects the frame. The cantilever beam may be bonded to the frame at a distal end of the cantilever. In certain cases the cantilever beam is flexible to avoid scraping the vessel wall during use. A filter mesh is attached to the expansion frame.

In use, the surgeon selects the tubular member, and the shaft with filter and cantilever beam adapted to extend through the tubular member. The cannula is inserted into a vessel. The tubular member is inserted into a port on the cannula. The filter is advanced into the vessel. The filter is deployed within the vessel. A procedure is then performed on the patient upstream of the filter, e.g., cross-clamping for CPB, CABG, valve repair, myocardial ablation, etc., wherein the procedure dislodges embolic material. Embolic material is captured by the filter. The cantilever beam and expansion frame flex when the tubular member is displaced inadvertently during the procedure. The filter and captured embolic material is then removed from the vessel.

BRIEF DESCRIPTION OF THE DRAWINGS

FIG. 1A depicts an embodiment of a cannula receiving a filter cartridge according to the present invention.

FIG. 1B depicts the filter expanded through a lumen of the cannula of FIG. 1A.

DETAILED DESCRIPTION

Figure 2A:
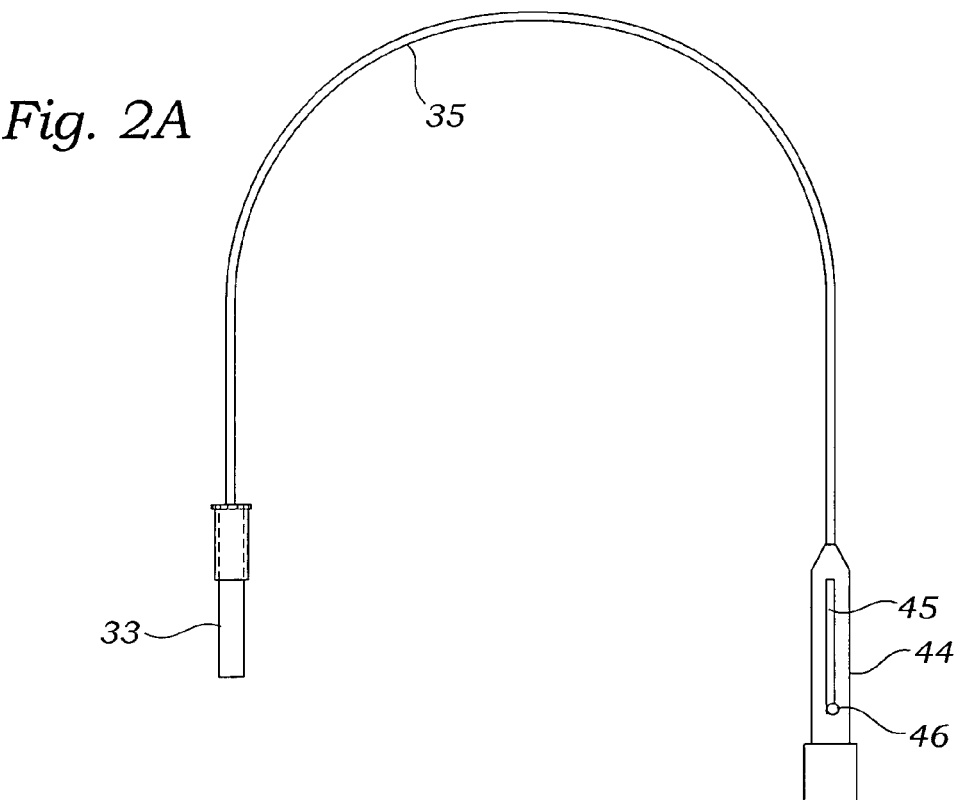
FIG. 2A depicts an embodiment of the flexible cable filter cartridge.

Although the devices and method disclosed herein are most useful in providing arterial cannulation and blood filtration during cardiovascular surgeries, the devices may be useful in other procedures, e.g., carotid endarterectomy, where blood filtration is desirable to prevent distal embolization.

Referring now to the drawings, an embodiment of the medical device suitable for blood filtration is depicted in FIG. 1A. The device generally comprises cannula 10 having a proximal end, distal end 11, and port 16 communicating with lumen 15. The device also includes port 20 located on an outer surface of cannula 10 and adjacent a distal region of cannula 10. Port 20 has a lumen 21 extending distally and communicating with a distal opening (not shown) that communicates with lumen 15 of cannula 10. Filter cartridge 30 has flexible tubular member 33 and flexible shaft 35 extending through the tubular member. An expansion frame is mounted on the distal end of shaft 35 and is capable of being contracted within tubular member 33 as shown in FIG. 1A or expanded as shown in FIG. 1B.

In use, tubular member 33, having the expansion frame in a contracted state, is inserted into port 20 and lumen 21 of the cannula. The proximal end of filter cartridge 30 is then activated to advance filter 40 through the distal port of cannula 10 as shown in FIG. 1B, thereby expanding frame 39. Filter mesh 40, for capturing vascular debris, is attached to expansion frame 39.

Figure 2B:
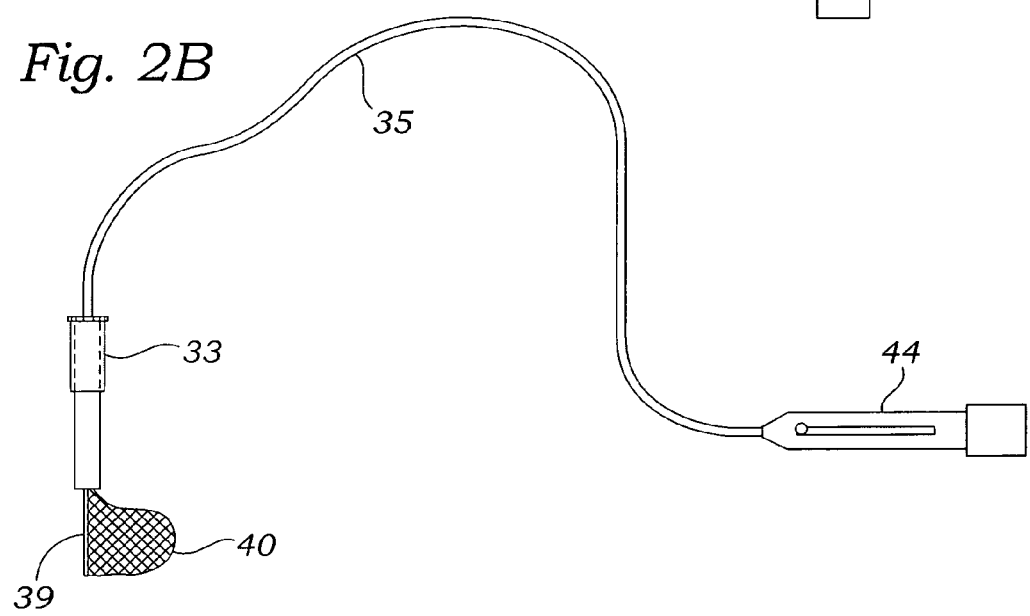
FIG. 2B depicts expansion of a filter by advancing a knob at the proximal region of the filter cartridge of FIG. 2A.

FIGS. 2A and 2B depict the filter activating mechanism at the proximal end of the flexible cable deployment mechanism. The proximal end includes handle 44 having slot 45 and knob 46 that is slideably mounted within the slot. To contract the expansion frame, knob 46 is withdrawn proximally, thereby collapsing the frame within tubular member 33 as shown in FIG. 2A. To expand the frame, knob 46 is advanced distally, thereby pushing expansion frame 39 out of tubular member 33.

Figure 3:
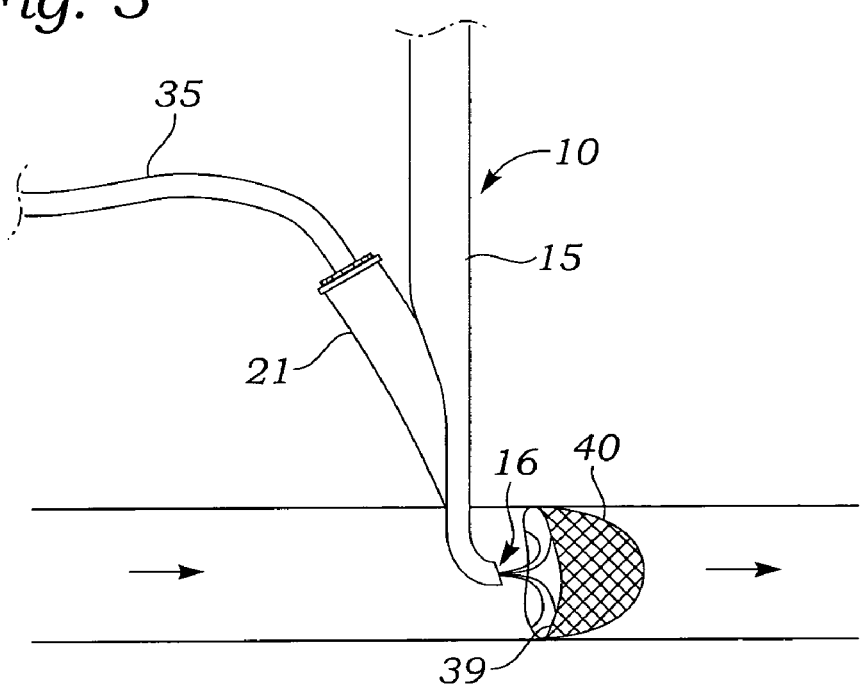
FIG. 3 depicts the cannula of FIG. 1B deployed within a vessel.

In use for performing cardiopulmonary bypass during cardiovascular surgeries, for example, the distal end of cannula 10 is first inserted in the ascending aorta (or other vessel) as depicted in FIG. 3. The distal region of the filter is inserted into lumen 21 of the cannula. Alternatively, the distal region of the filter is inserted into lumen 21 before insertion of cannula 10 into the aorta. Expansion frame 39 is then expanded distal to port 16 of the cannula. The proximal end of cannula 10 is attached to a bypass-oxygenator machine, and oxygenated blood is delivered through lumen 15 and port 16 to perfuse distal organs. After establishment of cardiopulmonary bypass, cardiovascular procedures, e.g., coronary artery bypass grafting, valvular repair or replacement, septal defect repair, and pulmonary stenosis surgeries, may be performed. Embolic debris generated during the surgeries is captured by mesh 40, thereby preventing distal embolization to peripheral organs. After completion of the surgeries, cardiopulmonary bypass is stopped, expansion frame 39 is collapsed, and mesh 40 with the entrapped embolic debris is removed from the cannula.

Figure 4:
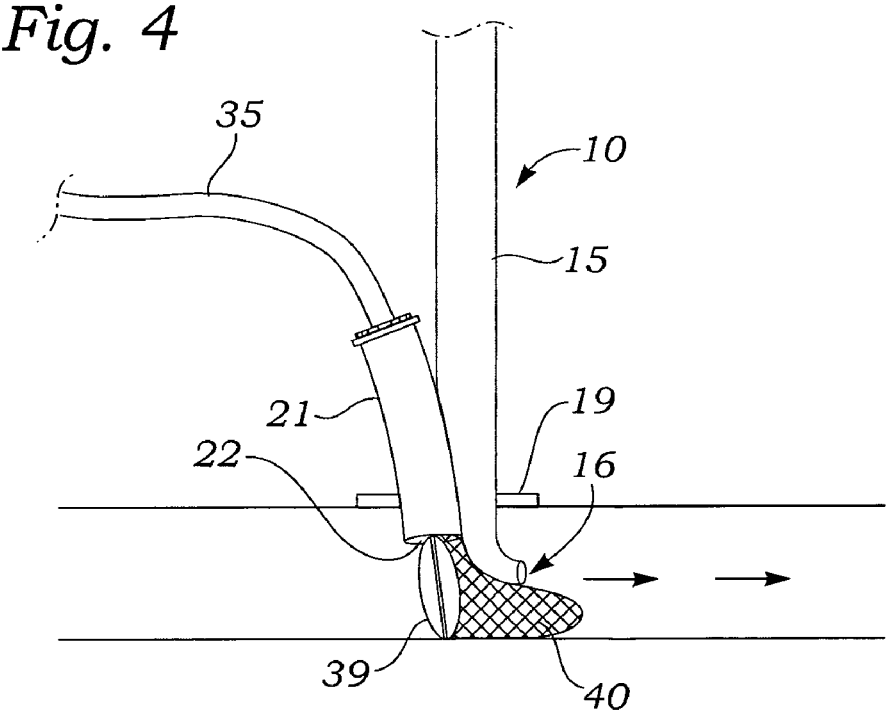
FIG. 4 depicts another embodiment of an arterial cannula deployed in the aorta.

FIG. 4 depicts another embodiment of the device suitable for performing arterial cannulation. The device includes cannula 10 and second lumen 21 located adjacent the cannula. Cannula 10 has lumen 15 communicating with distal port 16 that is adapted for perfusion of oxygenated blood. Lumen 21 communicates proximally with a port that is shaped to receive the filter cartridge, and distally with opening 22. In use, the distal end of cannula 10 is inserted into the aorta. Sutures may be placed on flange 19 to secure the cannula onto the vascular wall. A distal tubular member of a flexible filter cartridge, having expansion frame 39 in a contracted state, is inserted into the proximal port of lumen 21. Alternatively, the filter cartridge is inserted into lumen 21 prior to insertion of cannula 10 into the aorta. Expansion frame 39, which is attached to the distal end of shaft 35, is then expanded and deployed through port 22 to circumferentially cover the lumen of the aorta. Embolic debris generated during cardiovascular procedures is captured by mesh 40 and removed after the procedures. Flexible shaft 35, which extends proximal from port 20, is bendable and may be moved away from the cannula to avoid crowding of the surgical field and interference with the surgeon's activities.

Figure 5A:
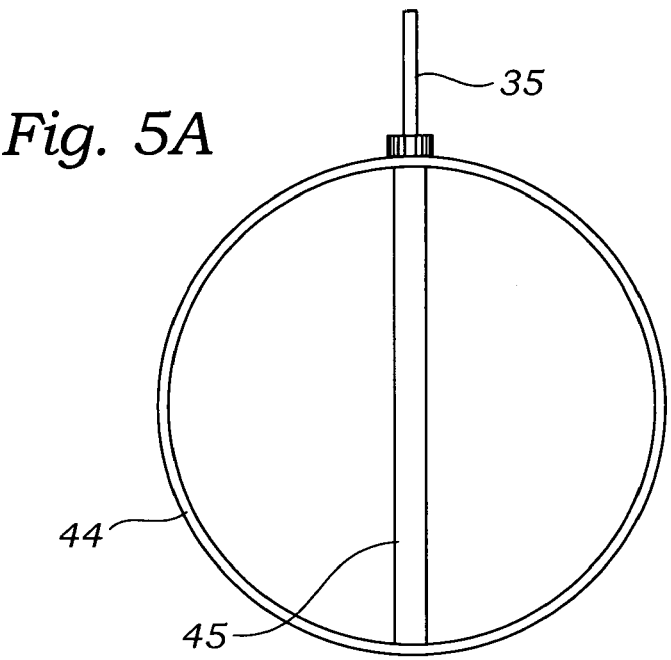
FIG. 5A depicts an embodiment of an expansion frame of the filter.
Figure 5B:
FIG. 5B depicts a cross-sectional view of a beam of the expansion frame of FIG. 5A.

FIG. 5A depicts an embodiment of the expansion frame suitable for use with the filter cartridge of FIG. 4. The expansion frame includes flexible circular ring 44, that is made of bio-compatible material, such as stainless steel or nitinol. The expansion frame also includes cantilever beam 45 that slideably extends from a distal end of shaft 35 and bisects ring 44 of the frame. The cantilever beam is bonded to ring 44 at a distal end of cantilever 45. FIG. 5B depicts a cross-sectional view of the cantilever beam of FIG. 5A which has an oval shape.

Figure 6A:
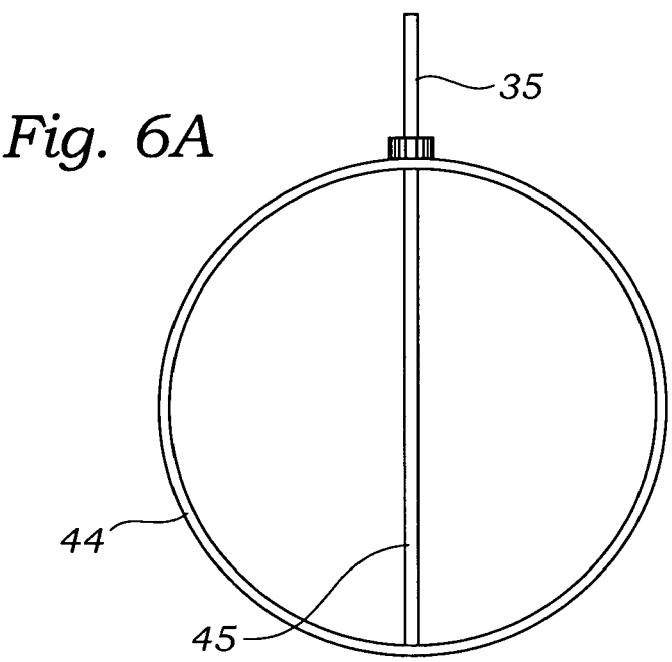
FIG. 6A depicts another embodiment of the expansion frame of the filter having a flexible cantilever beam.
Figure 6B:
FIG. 6B depicts a cross-sectional view of the flexible cantilever beam of FIG. 6A.

FIG. 6A depicts another embodiment of the expansion frame having cantilever beam 45 that bisects flexible circular ring 44. The cross-sectional view of the cantilever beam, which is circular, is shown in FIG. 6B. By reason of its cylindrical geometry, the cantilever beam is flexible, such that the beam bends when a force perpendicular to shaft 35 is applied. When the expansion frame is deployed in the vessel, the cantilever beam flexes to avoid scraping of the frame on the vessel wall when shaft 35 or the cannula is displaced. Alternatively, the cantilever beam of FIGS. 5A and 6A may be made of a more flexible materials, such as plastic, high density polyethylene (HDPE), low density polyethylene (LDPE), nylon, PEBAX, nitinol (optionally laser slotted or cut), laser cut nitinol, nylon, polyimide, or silicone. These materials may be supported by a length by stiffer materials such as stainless steel. This combination gives a hybrid cantilever tube (see FIG. 9J).

Figure 7A:
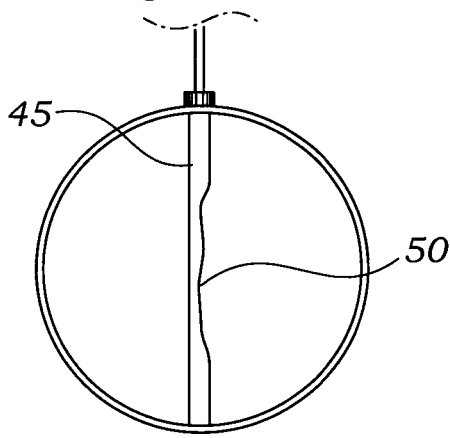
FIG. 7A depicts another embodiment of the flexible cantilever beam having a weakened region.
Figure 7B:
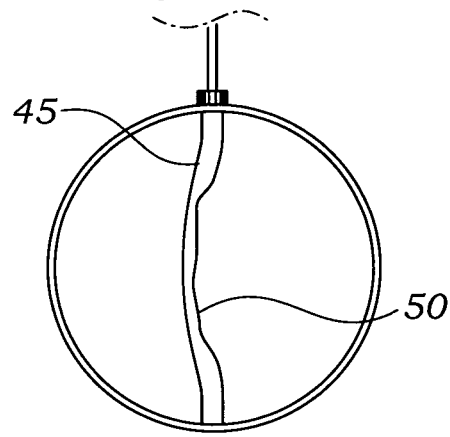
FIG. 7B depicts the flexible cantilever beam of FIG. 7A bending at its weakened region.
Figure 8A:
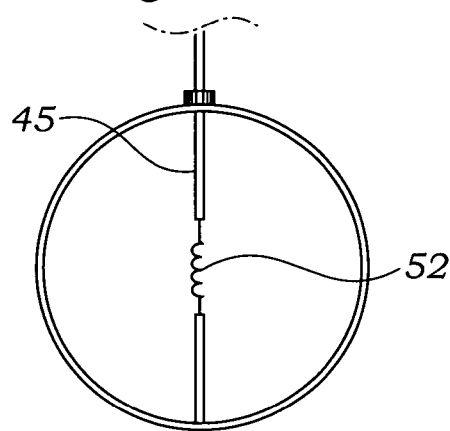
FIG. 8A depicts another embodiment of the flexible cantilever beam having a flexible spring.
Figure 8B:
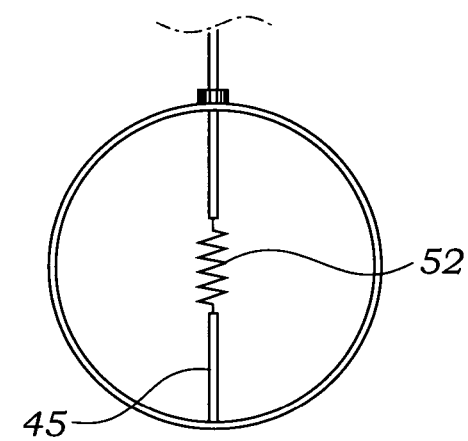
FIG. 8B depicts the flexible cantilever beam of FIG. 8A bending at the spring.
Figure 9A:
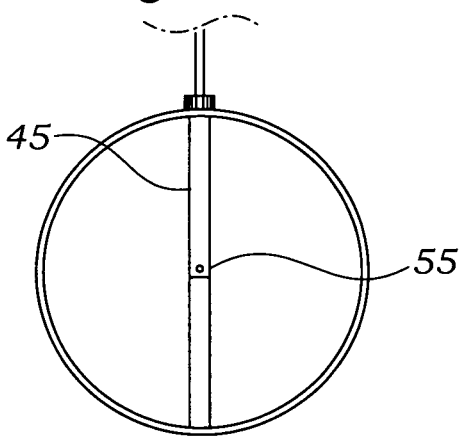
FIG. 9A depicts another embodiment of the flexible cantilever beam having a flexible hinge.
Figure 9B:
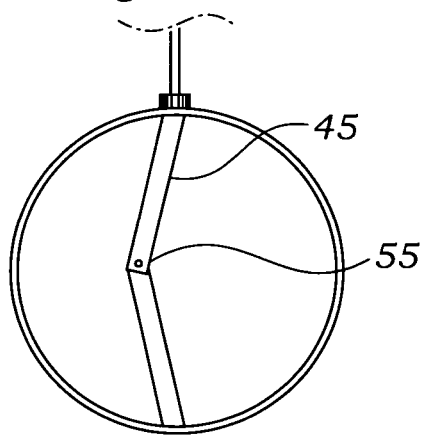
FIG. 9B depicts flexible cantilever beam of FIG. 9A bending at the flexible hinge.

FIG. 7A depicts another embodiment of a flexible cantilever beam having weakened region 50 in its mid-section. When the expansion frame is stressed, cantilever beam 45 is bendable at weakened region 50 as shown in FIG. 7B. In still another embodiment of the expansion frame, cantilever beam 45 includes flexible spring 52 that provides flexibility to cantilever beam 45 as shown in FIG. 8A. When the expansion frame is stressed, cantilever beam 45 is compressible and bendable at spring 52, resulting in slight deformation of the expansion frame and avoiding injury to the vessel wall. In still another embodiment of the expansion frame, cantilever beam 45 includes hinge 55 as shown in FIG. 9A. The cantilever beam is bendable at hinge 55 as shown in FIG. 9B.

Figure 9C:
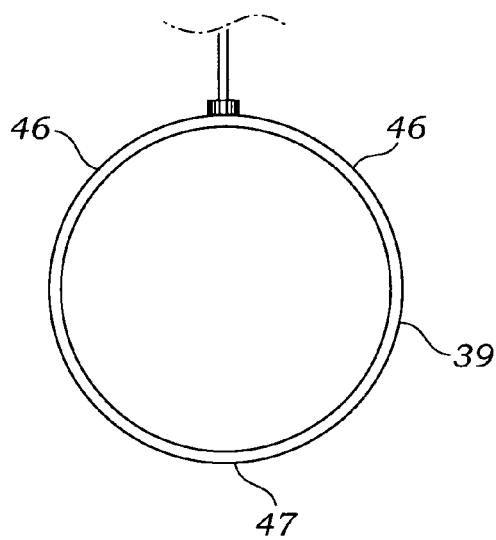
FIG. 9C depicts another embodiment of the expansion frame having differential stiffness around its circumference.
Figure 9D:
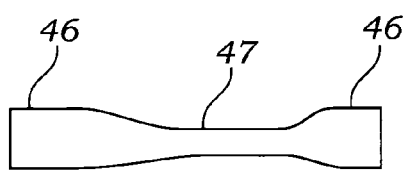
FIG. 9D depicts the material of the expansion frame lying flat before being formed into the expansion frame of FIG. 9C.
Figure 9E:
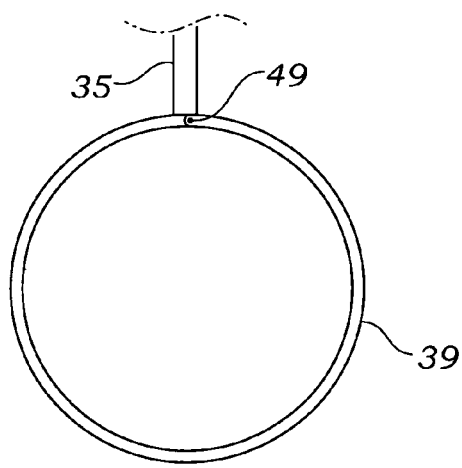
FIG. 9E depicts another embodiment of the expansion frame having a flexible hinge.
Figure 9F:
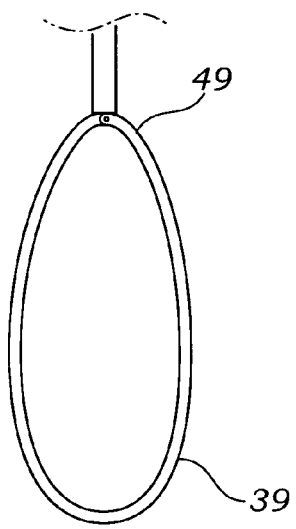
FIG. 9F depicts the expansion frame of FIG. 9E bending at the hinge.

FIG. 9C depicts another embodiments of expansion frame 39 having different thickness on different points of its expanded circumference to give different stiffness at different points on the circumference of the frame. For example, the thickness of frame 39 at point 46 is greater than the thickness at point 47, such that the frame is more stiff at point 46 and more flexible at point 47. This differential stiffness is accomplished by the construction shown in FIG. 9D, which depicts the material of the expansion frame lying flat before being formed into the expansion frame. FIG. 9E depicts another embodiment of the expansion frame having flexible hinge 49 at the joint between the distal end of shaft 35 and expansion frame 39. Flexible hinge 49 allows bending of expansion frame 39 as depicted in FIG. 9F, thereby allowing the frame to conform to the wall of a vessel when the vessel is stressed or when the vessel is irregular. FIG. 9G depicts another embodiment of the expansion frame, the flexibility of which is provided by having the frame constructed from flexible wire 51 attached to cantilever beam 45. Wire 51 includes first end 52 and second end 53, both of which are attached to cantilever beam 45. Cantilever beam 45 may be rigid or flexible. Wire 51 extends distally from first end 52, loops twice around the distal end of shaft 35, and attaches its second end 53 at cantilever 45. In this manner, the expansion frame is very flexible at segment 54 of the frame.

Figure 9H:
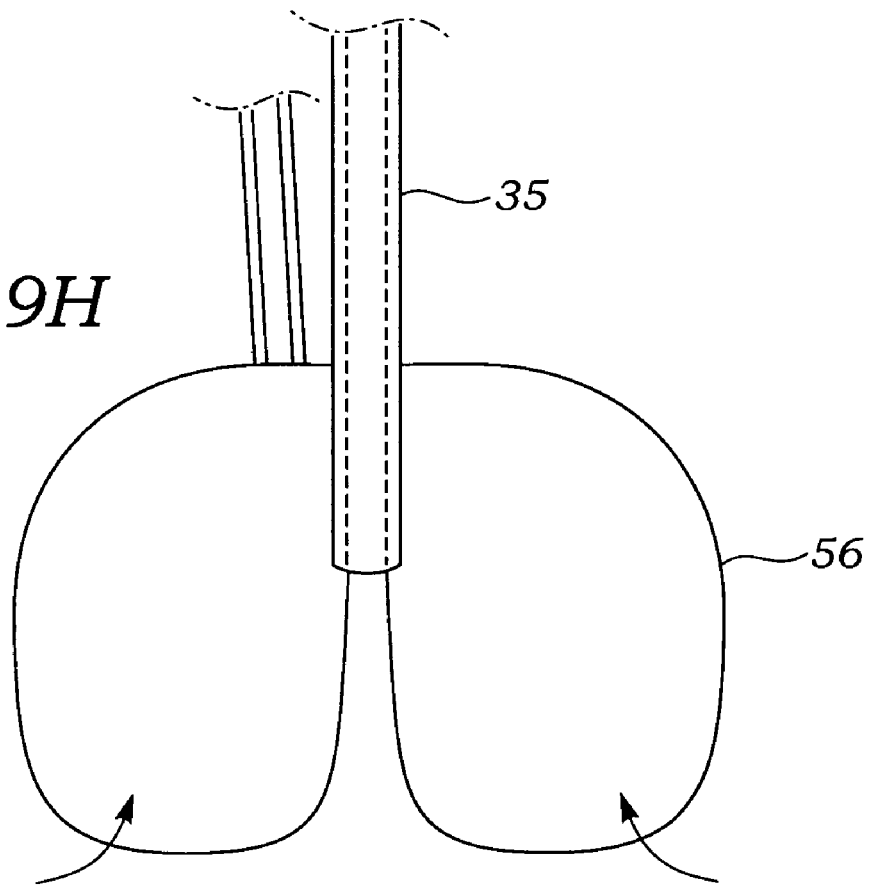
FIG. 9H depicts an expansion frame that closes by folding along a line that bisects the circle.
Figure 9I:
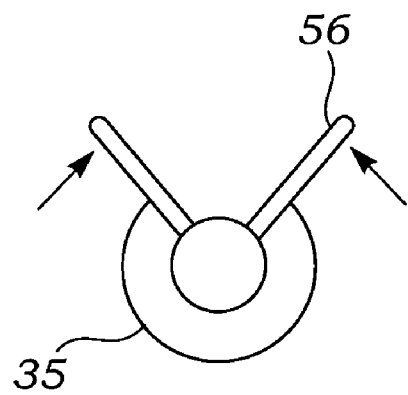
FIG. 9I depicts an end view of the expansion frame of FIG. 9H during closure.
Figure 9G:
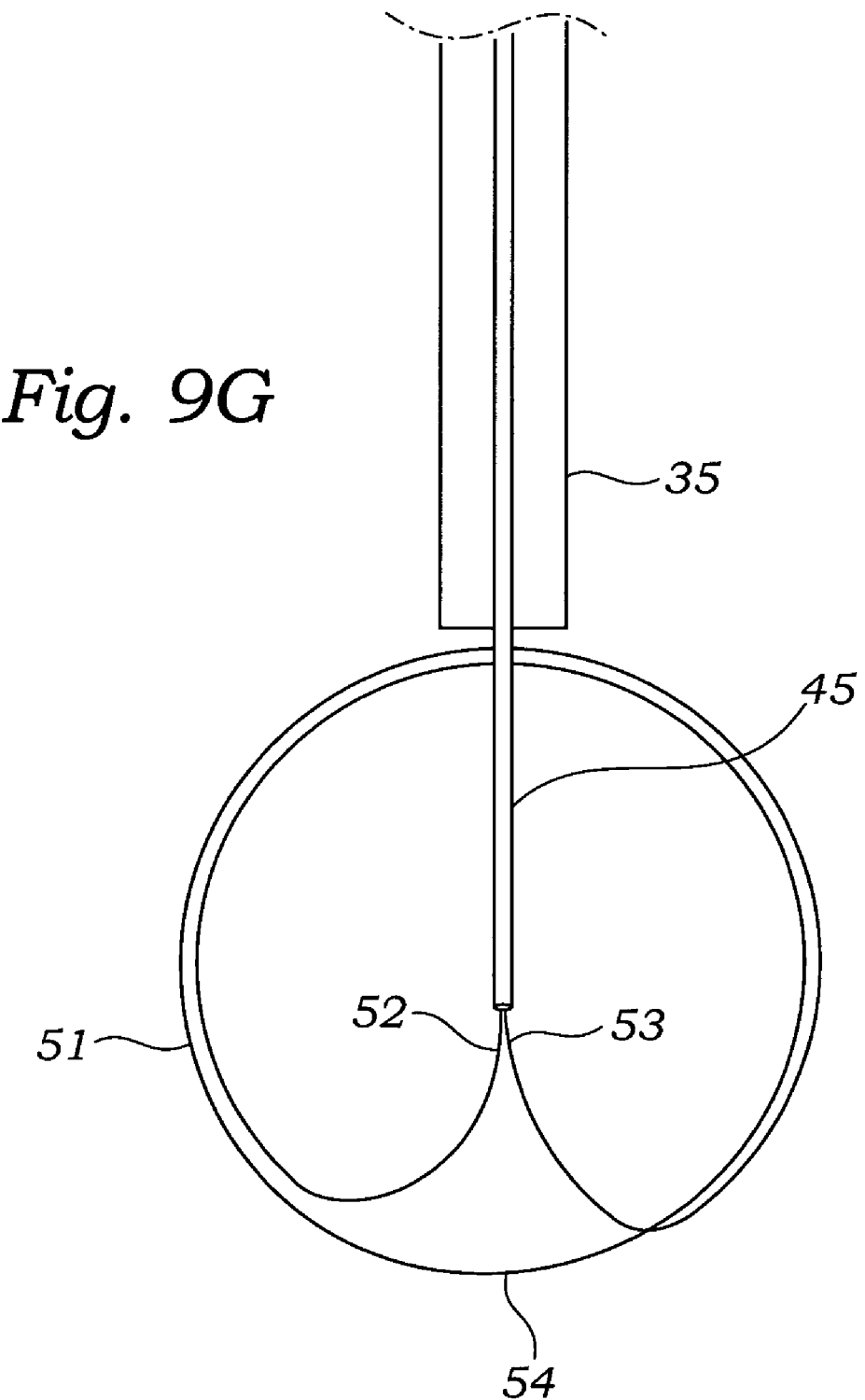
FIG. 9G depicts another embodiment of the expansion frame constructed of a flexible wire mounted on the cantilever beam.

In another embodiment shown in FIG. 9H, cannula 35 carries wire frame 56 at a distal end. The wire frame expands to cover the lumen of the vessel in use to filter blood passing through the lumen. The filter and frame 56 closes as shown in FIG. 9I when the procedure is finished by folding along a line that bisects the generally circular expansion frame.

Figure 9J:
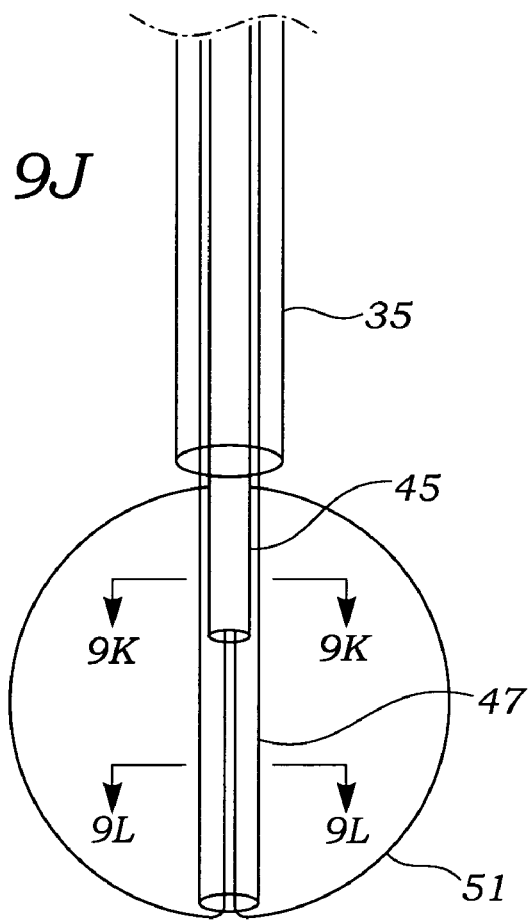
FIG. 9J depicts another embodiment of the expansion frame constructed of a flexible wire mounted on the cantilever beam with a flexible cantilever tube.
Figure 9K:
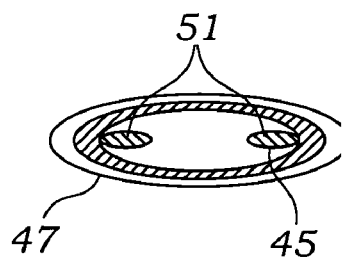
FIG. 9K shows a cross-section of the device of FIG. 9J taken through section line 9K—9K.
Figure 9L:
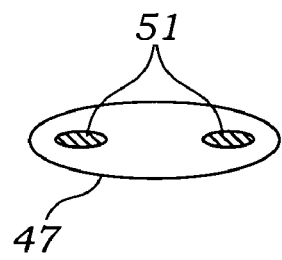
FIG. 9L shows a cross-section of the device of FIG. 9J taken through section line 9L—9L.

FIG. 9J depicts another embodiment of the expansion frame, the flexibility of which is provided by flexible cantilever tube 47. Flexible wire 51 is attached to cantilever beam 45, constructed from a relatively rigid material, e.g., hypotube. Wire 51 extends distally from cantilever beam 45, and loops around the distal end of shaft 35, and extends at its other end into cantilever beam 45. Flexible cantilever tube 47 covers cantilever beam 45, and extends to the distal portion of the expansion frame while covering wire 51. Flexible cantilever tube 47 may be constructed of materials such as plastic, high density polyethylene (HDPE), low density polyethylene (LDPE), nylon, PEBAX, nitinol (optionally laser slotted or cut), laser cut nitinol, nylon, polyimide, or silicone. The expansion frame is flexible beyond the cantilever beam 45. FIG. 9K shows a cross-section taken through section line 9K—9K, and FIG. 9L shows a cross-section taken through section line 9L—9L.

Figure 10:
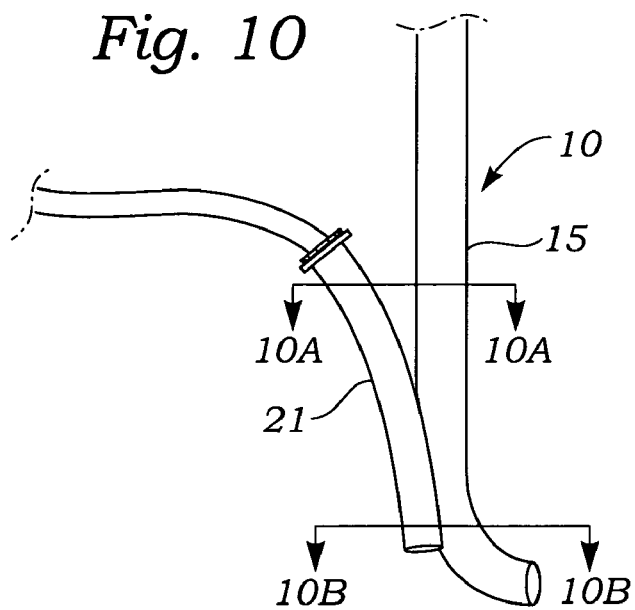
FIG. 10 depicts a distal region of an embodiment of an arterial cannula.
Figure 10A:
FIG. 10A depicts a cross-sectional view of the cannula of FIG. 10 through section line A—A.
Figure 10B:
FIG. 10B depicts a cross-sectional view of the cannula of FIG. 10 through section line B—B.

FIG. 10 depicts another embodiment of the device adapted for arterial cannulation and filtration. The device includes cannula 10 having lumen 15 and second lumen 21 that is adapted to receive a filter. The relationship between arterial lumen 15 and lumen 21 at different cross-sections of the device is shown in FIGS. 10A and 10B. In FIG. 10A, lumens 15 and 21 are both circular in cross-section. In FIG. 10B, lumen 21 is generally circular and lumen 15 that takes on an annular shape. This design is less desirable because the annular shape of the arterial return lumen may create turbulent flow and undesirable pressure changes as blood is delivered to the aorta during cardiopulmonary bypass.

Figure 11:
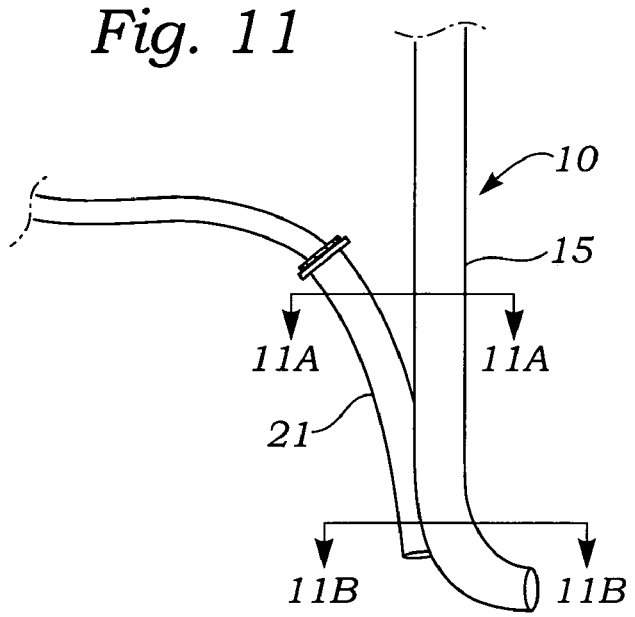
FIG. 11 depicts a distal region of another embodiment of an arterial cannula.
Figure 11A:
FIG. 11A depicts a cross-sectional view of the cannula of FIG. 11 through section line A—A.
Figure 11B:
FIG. 11B depicts a cross-sectional view of the cannula of FIG. 11 through section line B—B.

In FIG. 11, lumen 21 which is shaped to receive a filter is located adjacent to lumen 15 which is adapted for perfusion of blood. Lumens 15 and 21 are both circular through section-line A—A as shown in FIG. 11A. In FIG. 11B, lumen 21, having an annular shape, is located adjacent to circular lumen 15. This design reduces turbulent blood flow and undesired pressure changes.

The length of the cannula will generally be between approximately 20 and 80 centimeters, preferably between approximately 25 and 40 centimeters. The length of the flexible cable filter will generally be between approximately 50 and 130 centimeters, preferably between approximately 70 to 100 centimeters. The inner diameter of the cannula will generally be between approximately 0.5 and 2.0 centimeters, preferably approximately 0.8 and 1.5 centimeters for use in the aorta. The diameter of the expansion frame when deployed will generally be between 2 and 6 centimeters, preferably approximately 3 and 5 centimeters for use in the aorta. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for purposes of clarity of understanding, been described in some detail by way of illustration and example, it will be obvious that certain changes and modifications may be practiced which will still fall within the scope of the appended claim. It will also be understood that each feature of each embodiment discussed herein, and of each reference cited herein, can be used in combination with the features of any other embodiment.

What is claimed is:
1. A filter, comprising;
   a tubular member;

a shaft extending through the tubular member;

an expansion frame mounted on the distal end of the shaft, the expansion frame expandable between a contracted condition and an expanded condition, the expansion frame including a flexible ring;

a flexible cantilever beam having a first cross-section, wherein the cantilever beam is configured to slideably extend from a distal end of the shaft and contacts the expansion frame at a first point on the cantilever beam and at a distal end of the cantilever beam, the cantilever beam having a weakened region with a second cross-section, wherein the second cross-section is smaller than the first cross-section; and a filter mesh attached to the expansion frame.

2. The filter of claim 1, wherein the flexible cantilever beam comprises a nitinol tube of generally cylindrical shape.

3. The filter of claim 1, wherein the flexible cantilever beam is constructed from a composite of materials.

4. The filter of claim 1, wherein the flexible cantilever beam is constructed of bare wire, plastic tube, and metal outer sheath.

5. A method for filtering blood, comprising:

providing a tubular member, a shaft extending through the tubular member, an expansion frame mounted on the distal end of the shaft, a flexible cantilever beam having a first cross-section, wherein the cantilever beam slideably extends from a distal end of the shaft and contacts the expansion frame at a first point on the cantilever beam and at a distal end of the cantilever beam, and wherein the cantilever beam has a weakened region with a second cross-section, wherein the second cross-section is smaller than the first cross-section, and a filter mesh attached to the expansion frame;

inserting a cannula into a vessel;

inserting the tubular member into a port on the cannula;

advancing the filter mesh into the vessel;

deploying the filter mesh within the vessel; and removing the filter mesh from the vessel.

* * * * *